(12) United States Patent
Hurwitz et al.

(10) Patent No.: US 10,154,693 B2
(45) Date of Patent: Dec. 18, 2018

(54) METHOD AND SYSTEM FOR PRODUCING OXYGEN-RICH VAPOR DERIVED FROM HERB-BASED PLANTS

(71) Applicants: Bruce Hurwitz, Simpsonville, SC (US); Linda Simon, Herndon, VA (US)

(72) Inventors: Bruce Hurwitz, Simpsonville, SC (US); Linda Simon, Herndon, VA (US)

( * ) Notice: Subject to any disclaimer, the term of this patent is extended or adjusted under 35 U.S.C. 154(b) by 241 days.

(21) Appl. No.: 15/260,072

(22) Filed: Sep. 8, 2016

(65) Prior Publication Data
US 2018/0064168 A1    Mar. 8, 2018

(51) Int. Cl.
| | |
|---|---|
| A61K 9/00 | (2006.01) |
| A24F 47/00 | (2006.01) |
| A24F 1/30 | (2006.01) |
| A24B 15/16 | (2006.01) |
| A61K 36/67 | (2006.01) |
| A61K 33/00 | (2006.01) |
| A61M 11/04 | (2006.01) |
| A61M 16/10 | (2006.01) |
| A61M 16/12 | (2006.01) |
| A61M 15/08 | (2006.01) |

(52) U.S. Cl.
CPC ............ *A24F 47/008* (2013.01); *A24B 15/16* (2013.01); *A24F 1/30* (2013.01); *A61K 33/00* (2013.01); *A61K 36/67* (2013.01); *A61M 11/042* (2014.02); *A61M 16/108* (2014.02); *A61M 16/125* (2014.02); *A61K 9/007* (2013.01); *A61M 15/08* (2013.01); *A61M 2202/0208* (2013.01)

(58) Field of Classification Search
USPC ............. 422/120, 123; 131/328; 203/40, 91; 604/23, 99.02
See application file for complete search history.

(56) References Cited

U.S. PATENT DOCUMENTS

| | | | |
|---|---|---|---|
| 2007/0068523 A1* | 3/2007 | Fishman | A61M 16/0051 128/203.12 |
| 2012/0124704 A1* | 5/2012 | Szymanowski | A23F 3/34 800/298 |
| 2013/0298905 A1* | 11/2013 | Levin | A24F 47/008 128/202.21 |
| 2014/0057027 A1* | 2/2014 | Ablett | A23B 4/052 426/314 |

(Continued)

FOREIGN PATENT DOCUMENTS

RU    2536894    * 12/2014    ............... A23L 2/00

*Primary Examiner* — Nina Bhat (57) ABSTRACT

A method and system for producing oxygen-rich vapor derived from herb-based plants and extracts from said herb-based plants for consumption by individuals. The method includes transferring a first portion of a base quantity of oxygen-enriched vapor form a volumetric container into a vaporization device. The vaporization device retains an herb-based plant material. The herb-based plant material is used in conjunction with the first portion to produce herb-infused vapor through an atomization process. The herb-infused vapor is then permeated into a mixing chamber with a second portion of the base quantity of oxygen-enriched vapor from the volumetric container. The second portion is then mixed with the herb-infused vapor in order to formulate an oxygen-infused herb vapor. The oxygen-infused herb vapor is then dispensed from the mixing chamber for individual consumption.

8 Claims, 8 Drawing Sheets

(56) References Cited

U.S. PATENT DOCUMENTS

| | | | |
|---|---|---|---|
| 2015/0196613 A1* | 7/2015 | Ahmad | A61K 36/88 |
| | | | 424/725 |
| 2016/0193266 A1* | 7/2016 | Ablett | A61K 36/185 |
| | | | 424/439 |
| 2016/0279184 A1* | 9/2016 | Xing | A61K 36/67 |
| 2016/0331913 A1* | 11/2016 | Bourque | A61M 11/02 |
| 2016/0346339 A1* | 12/2016 | Finley | A61K 31/352 |
| 2017/0295843 A1* | 10/2017 | Storch | A61M 11/041 |
| 2018/0027872 A1* | 2/2018 | Galaviz, Jr. | A24F 7/02 |
| 2018/0070635 A1* | 3/2018 | Litten | A24F 47/008 |
| 2018/0168223 A1* | 6/2018 | Zinovik | A24F 47/008 |

* cited by examiner

METHOD AND SYSTEM FOR PRODUCING OXYGEN-RICH VAPOR DERIVED FROM HERB-BASED PLANTS

FIELD OF THE INVENTION

The present invention relates generally to methods and systems for producing, distributing, and consuming herb-based plants and extracts from said herb-based plants. More specifically, the present invention is a method for producing an oxygen-rich vapor derived from herb-based plants or extracts from said herb-based plants in order to deliver a heightened experience to the user.

BACKGROUND OF THE INVENTION

Extraction of ingredients from botanicals has produced a wide variety of substances and compounds that are beneficial within and outside the medical field. More specifically, said ingredients may be consumed in order induce mental and physical effects for the individual. One example is the herb kava kava, a crop indigenous to the western Pacific. Kava kava, when consumed, produces effects with sedative, anesthetic, and entheogenic properties. In recent years, kava kava and many other herb-based plants have become extremely popular within and outside of the medical field. Non-medical use refers to said herb-based plants being used for recreational purposes, consumption for the purpose of inducing the associated psychoactive effects without medical justification. In order to receive the mental and physical effects of these herb-based substances, the plant matter or extracts from said plant matter must be consumed in a specific fashion. One method includes infusing edible goods with oils derived from the plant matter and ingesting the final product. The most popular method includes burning or vaporizing the plant matter and inhaling the resulting smoke, colloquially referred to as smoking.

The present invention provides an alternative means for consuming herb-based plants and products derived from said herb-based plants. More specifically, the present invention is a method for producing a hyper-oxygenated herb-infused vapor for recreational and medical purposes. When consumed, the hyper-oxygenated herb-infused vapor produces a heightened experience to the user including increasing alertness, relieving tiredness, and improving athletic abilities. For recreational use, the present invention enables the user to consume the hyper-oxygenated herb-infused vapor directly from the source or from a mylar-like balloon, thus allowing for the consumption of the hyper-oxygenated herb-infused vapor in social settings such as a lounge or a club.

DETAIL DESCRIPTIONS OF THE INVENTION

All illustrations of the drawings are for the purpose of describing selected versions of the present invention and are not intended to limit the scope of the present invention.

The present invention is a method and system for producing oxygen-enriched vapor derived from herb-based plants and extracts from said herb-based plants. An example of the herb-based plant is kava kava. The oxygen-enriched vapor produces a heightened experience to the consumer. Additionally, the present invention provides a means for mass-producing and serving the oxygen-enriched vapor to a large number of individuals in a short amount of time.

Figure 1:
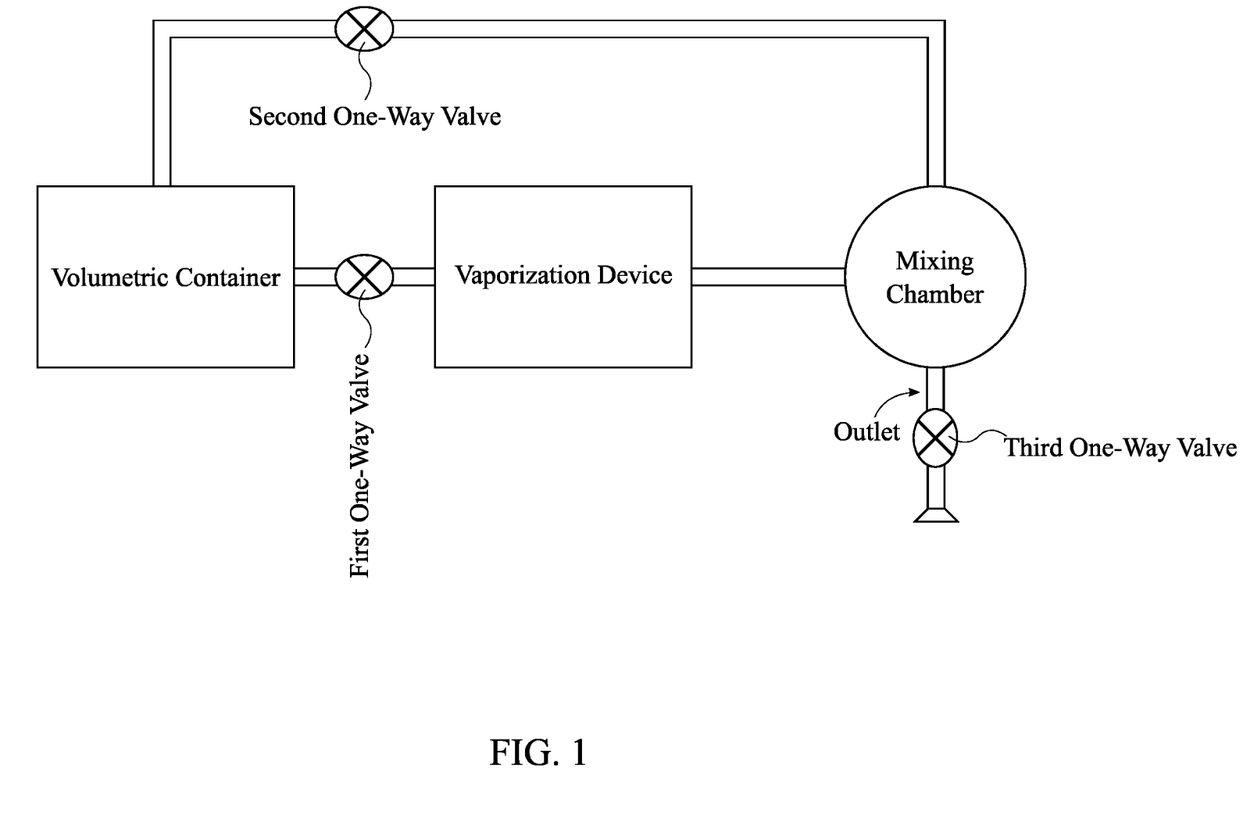
FIG. 1 is a schematic diagram of the present invention.

The system portion comprises the physical components of the present invention. More specifically, the system portion includes a volumetric container, a vaporization device, and a mixing chamber as seen in FIG. 1. The volumetric container stores a base quantity of oxygen-enriched vapor, preferably at a relatively high pressure (Step A). The volumetric container is preferably an oxygen condenser. Oxygen condensers are able to produce oxygen-enriched vapor from ambient air and therefore highly portable. The consumption, inhalation, of air with significantly higher concentrations of oxygen has been claimed to enhance an individual's health and well-being. Some of the main benefits include increasing alertness, relieving tiredness, relaxing the body, and improving athletic abilities. The vaporization device is a device that atomizes an herb-based plant material or an herb-based plant extract in order to release desired active ingredients. The vaporization device is in selective fluid communication with the volumetric container through a first one-way valve, wherein the first one-way valve allows fluid to flow only in a single direction, out of the volumetric container (Step B). The selective fluid communication allows for the complete control in relation to the amount of oxygen-enriched vapor flowing into the vaporization device. A variety of different devices may be used for the vaporization device component of the present invention.

The mixing chamber is a device which receives and mixes at least two streams of fluids. In relation to the present invention, the mixing chamber receives fluid from the volumetric container, the vaporization device, and mixes the fluids. More specifically, the mixing chamber is in selective fluid communication with the volumetric container through a second one-way valve. Additionally, the mixing chamber is in direct fluid communication with the vaporization device (Step C). A variety of devices may be used for the mixing chamber.

Figure 3:
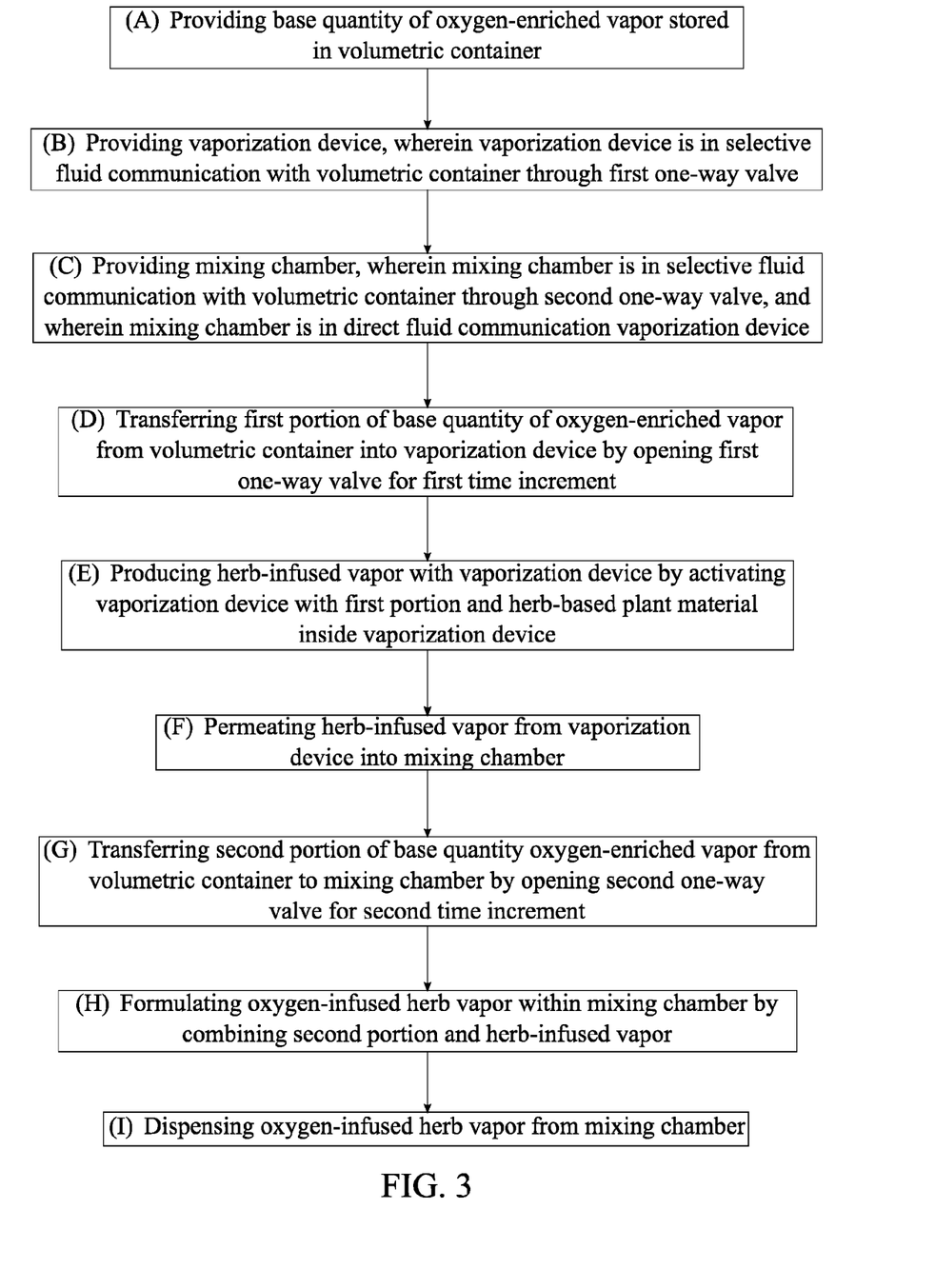
FIG. 3 is a flowchart depicting the overall process of the present invention.

Referring to FIG. 3, the overall process of the present invention delineates the steps necessary to produce oxygen-infused herb vapor with the aforementioned components. First, a first portion of the base quantity of oxygen-enriched vapor is transferred from the volumetric container into the vaporization device by opening the first one-way valve for a first time increment (Step D). For this process, it is important that the pressure within the volumetric container is greater than that of the vaporization device in order to ensure adequate volumetric flow from the volumetric container to the vaporization device. Next, herb-infused vapor is produced with the vaporization device by activating the vaporization device with the first portion and the herb-based plant material inside the vaporization device (Step E). This step includes passing a heated oxygen-enriched vapor through the herb-based plant material in order to atomize the herb-based plant material, thus releasing active ingredients. Because the vaporization device is direct fluid communication with the mixing chamber, the herb-infused vapor then permeates from the vaporization device into the mixing chamber (Step F).

Continuing the overall process, a second portion of the base quantity of oxygen-enriched vapor is transferred from the volumetric container to the mixing chamber by opening the second one-way valve for a second time increment (Step G). The additional quantity of the oxygen-enriched vapor is used to raise the oxygen levels of the herb-infused vapor. Varying the second time increment allows for direct and proportional control of the oxygen levels in the final product of the present invention, i.e. the oxygen-infused herb vapor. In particular, increasing the second time increment yields a higher oxygen content in the oxygen-infused herb vapor and vice versa. Then, the second portion mixes with the herb-infused vapor within the mixing chamber in order to formulate the oxygen-infused herb vapor (Step H). Finally, the oxygen-infused herb vapor is dispensed from the mixing chamber for consumption by individuals (Step I).

Figure 4:
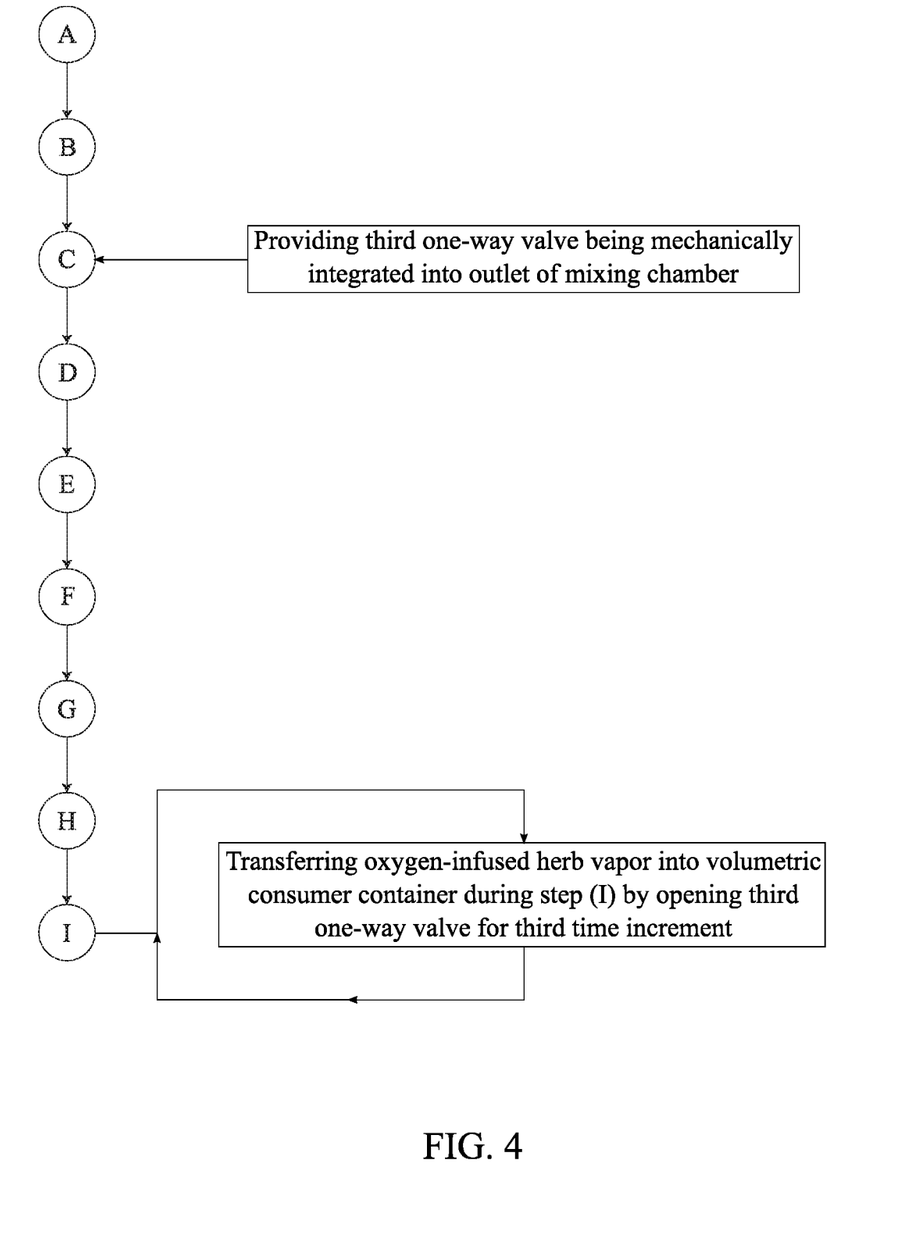
FIG. 4 is a flowchart depicting the steps necessary to disperse a quantity of the oxygen-infused herb vapor into a volumetric consumer container.

Because the final product is in the form of vapor, the present invention utilizes a volumetric consumer container in order to store and disperse the oxygen-infused herb vapor to individuals. More specifically, this is implemented through the use of a third one-way valve, wherein the third one-way valve is mechanically integrated into an outlet of the mixing chamber. The third one-way valve allows for dynamic control over the amount of oxygen-infused herb vapor being dispensed during Step I. The oxygen-infused herb vapor is transferred into the volumetric consumer container during Step I by opening the third one-way valve for a third time increment, depicted in FIG. 4. Increasing the third time increment yields a higher volume of the oxygen-infused herb vapor and vice versa.

Figure 5:
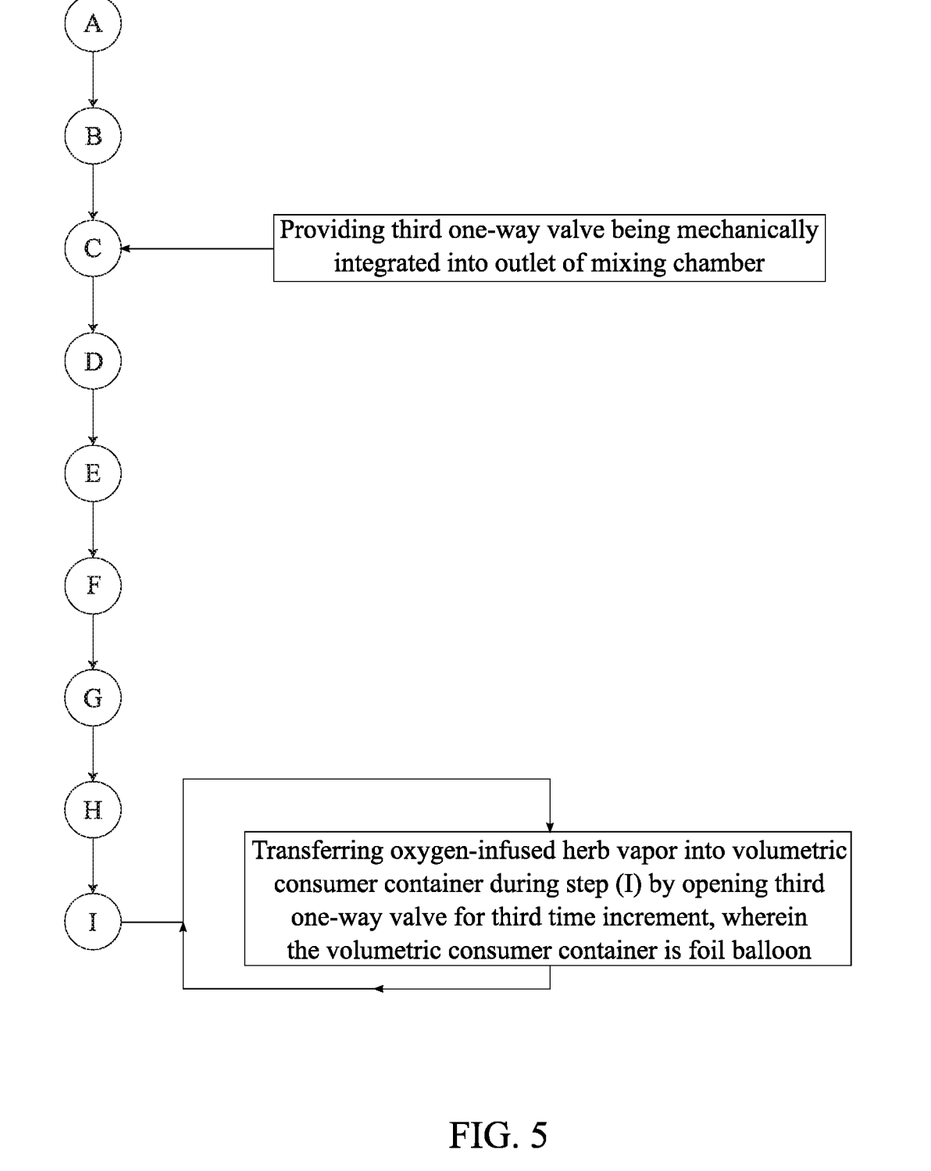
FIG. 5 is a flowchart depicting the steps necessary to disperse a quantity of the oxygen-infused herb vapor into a foil balloon.
Figure 6:
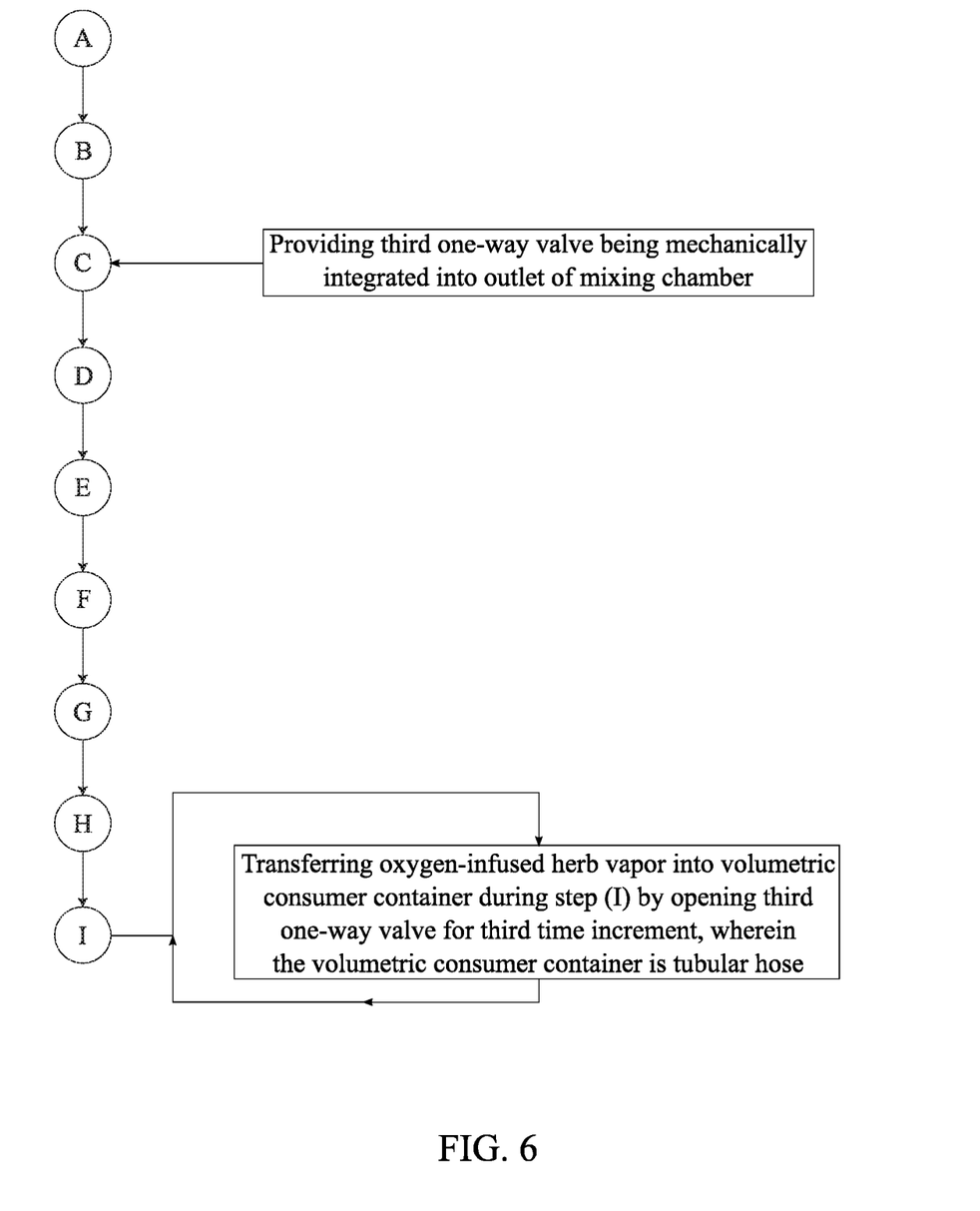
FIG. 6 is a flowchart depicting the steps necessary to disperse a quantity of the oxygen-infused herb vapor into a tubular hose.

The oxygen-infused herb vapor may be served or consumed through a variety of means. In one embodiment of the present invention, referring to FIG. 5, the volumetric consumer container is a foil balloon, similar to mylar balloons. The foil balloon may include a re-sealable mouthpiece in order to allow an individual to inhale the oxygen-infused herb vapor in separate portions. Additionally, the foil balloon may be implemented in a range of sizes. This allows for the distribution of the final product of the present invention. In another embodiment of the present invention, referring to FIG. 6, the volumetric consumer container is a tubular hose, similar to a hose from a hookah assembly. The tubular hose allows for direct consumption of the oxygen-infused herb vapor from the mixing chamber, similar to a hookah assembly setup.

An automatic valve or a manual valve may be used for the first one-way valve, the second one-way valve, and the third one-way valve. Utilizing an automatic valve allows for the remote and automatic control of the flow of fluid within the present invention, thus requiring little to no external input. Through the use of automatic valves, the present invention may be operated completely electronically by an external computing device. Alternatively, utilizing manual valves allows for manual control over the present invention.

Figure 2:
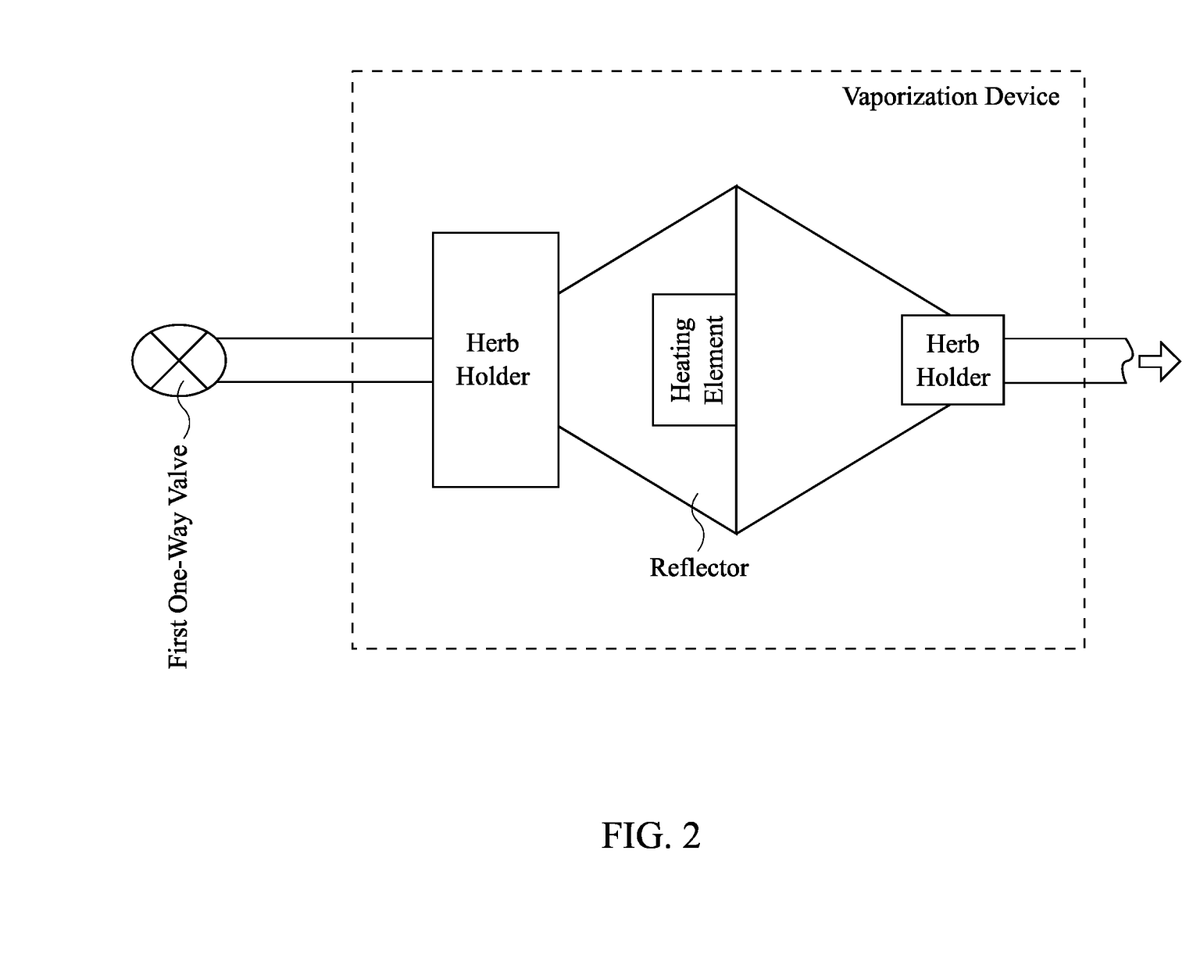
FIG. 2 is a detailed schematic diagram of the vaporization device.

Referring to FIG. 2, in the preferred embodiment of the present invention, the vaporization device includes a fan, a heating element, an herb holder, and a reflector. The fan, the heating element, the herb holder, and the reflector are in direct fluid communication with each other. In other words, gasses within the vaporization device are able to flow around the aforementioned components freely. Additionally, the fan is in selective fluid communication with the volumetric container through the first one-way valve, thus regulating and pumping the oxygen-enriched vapor into the vaporization device. The heating element converts electrical energy into heat. A variety of technologies may be used for the heating element including resistance wire, etched foil, ceramic-based heating elements, and silicone rubber heating elements to name a few non-limited examples. The produced heat is used for the atomization of the herb-based plant material or the herb-based plant extract. The herb holder receives and retains the herb-based plant material or herb-based plant extract. In one embodiment, the herb holder also includes a mixer for breaking down large pieces of the herb-based plant material in order to increase contact surfaces, thus increasing the efficiency of the vaporization device. The reflector contains a highly reflective surface that is used to focus the heat produced by the heating element onto the oxygen-enriched vapor, again to increase the efficiency of the vaporization device. As a result, the reflector is positioned around the heating element.

Figure 7:
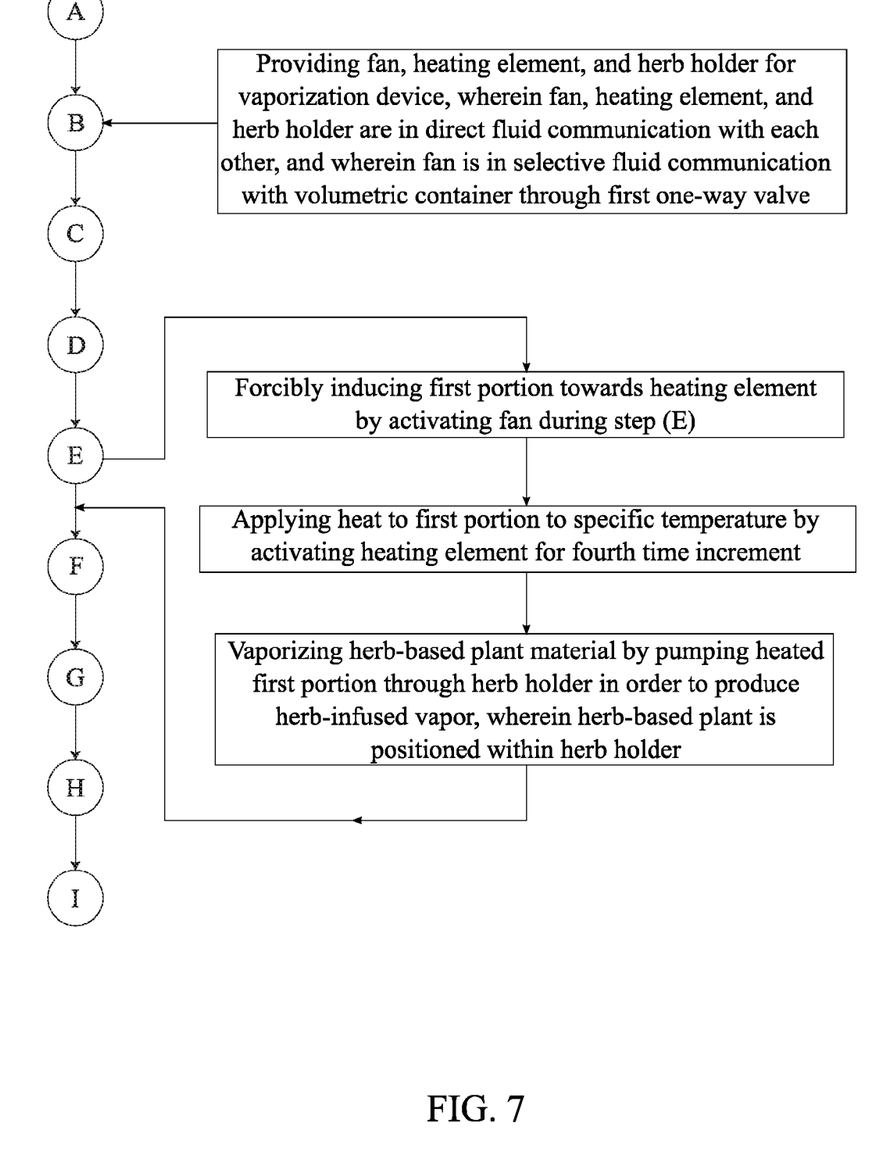
FIG. 7 is a flowchart depicting the steps necessary to produce herb-infused vapor by the vaporization device.
Figure 8:
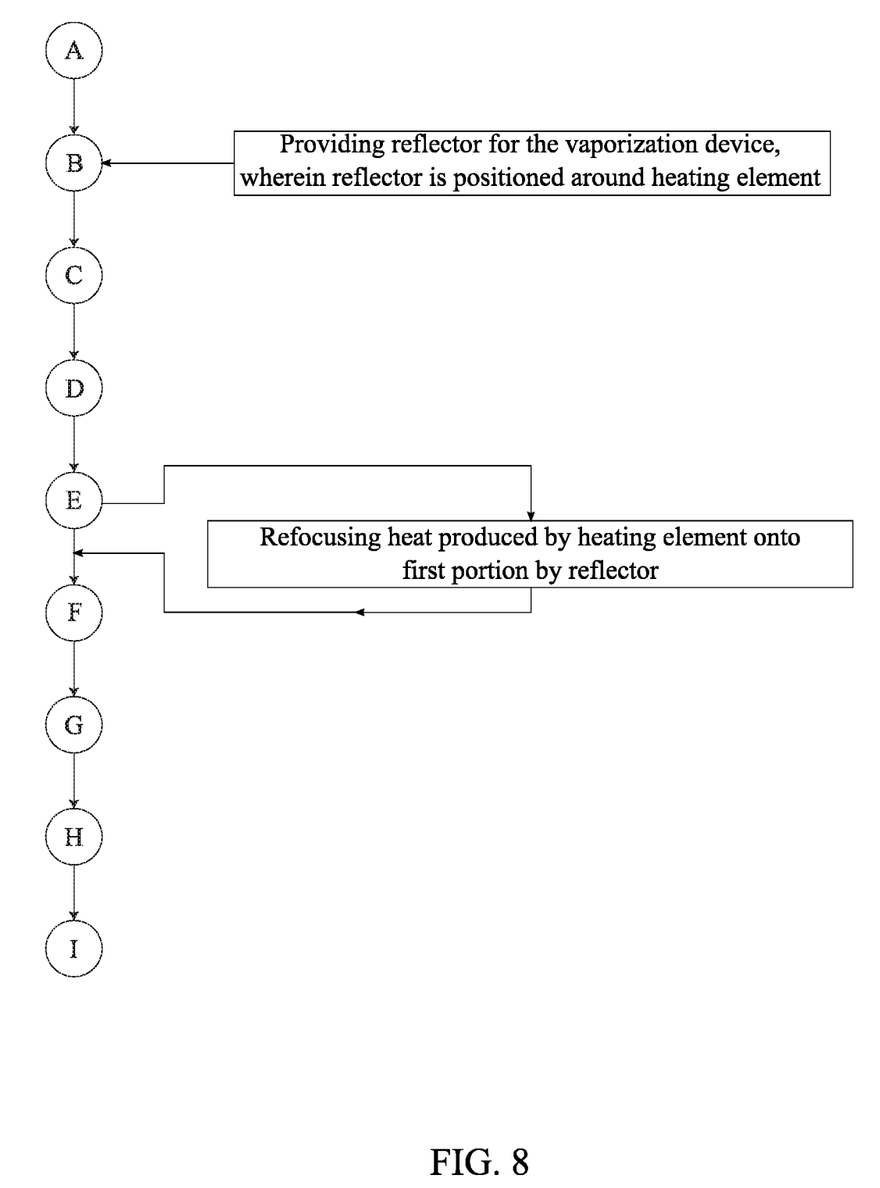
FIG. 8 is a flowchart depicting the steps necessary to apply heat to the oxygen-enriched vapor by a reflector.

Referring to FIG. 7, in order to produce the herb-infused vapor during Step E includes first, forcibly inducing the first portion towards the heating element. Next, heat is applied to the first portion to a specific temperature by activating the heating element for a fourth time increment. Varying the fourth time increment controls the specific temperature of the first portion. Additionally, the heat produced by the heating element is further refocused onto the first portion by the reflector. Finally, the herb-based plant is vaporized by pumping the heated first portion through the herb holder in order to produce the herb-infused vapor, wherein the herb-based plant material is positioned within the herb holder. It is important to note that a length of the first time increment is inversely proportionate to a length of the fourth time increment.

Although the invention has been explained in relation to its preferred embodiment, it is to be understood that many other possible modifications and variations can be made without departing from the spirit and scope of the invention as hereinafter claimed.

What is claimed is:

1. A method for producing oxygen-rich vapor derived from herb-based plants and extracts from said herb-based plants comprises the steps of:
   (A) providing a base quantity of oxygen-enriched vapor stored in a volumetric container;
   (B) providing a vaporization device, wherein the vaporization device is in selective fluid communication with the volumetric container through a first one-way valve;
   (C) providing a mixing chamber, wherein the mixing chamber is in selective fluid communication with the volumetric container through a second one-way valve, and wherein the mixing chamber is in direct fluid communication the vaporization device;
   (D) transferring a first portion of the base quantity of the oxygen-enriched vapor from the volumetric container into the vaporization device by opening the first one-way valve for a first time increment;
   (E) producing herb-infused vapor with the vaporization device by activating the vaporization device with the first portion and an herb-based plant material inside the vaporization device;
   (F) permeating the herb-infused vapor from the vaporization device into the mixing chamber;
   (G) transferring a second portion of the base quantity of the oxygen-enriched vapor from the volumetric container to the mixing chamber by opening the second one-way valve for a second time increment;

(H) formulating an oxygen-infused herb vapor within the mixing chamber by combining the second portion and the herb-infused vapor; and (I) dispensing the oxygen-infused herb vapor from the mixing chamber.

2. The method for producing oxygen-rich vapor derived from herb-based plants and extracts from said herb-based plants as claimed in claim 1 comprises the steps of:

providing a third one-way valve being mechanically integrated into an outlet of the mixing chamber; and transferring oxygen-infused herb vapor into a volumetric consumer container during step (I) by opening the third one-way valve for a third time increment.

3. The method for producing oxygen-rich vapor derived from herb-based plants and extracts from said herb-based plants as claimed in claim 2, wherein the volumetric consumer container is a foil balloon.

4. The method for producing oxygen-rich vapor derived from herb-based plants and extracts from said herb-based plants as claimed in claim 2, wherein the volumetric consumer container is a tubular hose.

5. The method for producing oxygen-rich vapor derived from herb-based plants and extracts from said herb-based plants as claimed in claim 1, wherein the herb-based plant material is an herb-based plant extract.

6. The method for producing oxygen-rich vapor derived from herb-based plants and extracts from said herb-based plants as claimed in claim 1 comprises the steps of:

providing a fan, a heating element, and an herb holder for the vaporization device, wherein the fan, the heating element, and the herb holder are in direct fluid communication with each other, and wherein the fan is in selective fluid communication with the volumetric container through the first one-way valve;

forcibly inducing the first portion towards the heating element by activating the fan during step (E);

applying heat to the first portion to a specific temperature by activating the heating element for a fourth time increment; and vaporizing the herb-based plant material by pumping the heated first portion through the herb holder in order to produce the herb-infused vapor, wherein the herb-based plant material is positioned within the herb holder.

7. The method for producing oxygen-rich vapor derived from herb-based plants and extracts from said herb-based plants as claimed in claim 6 comprises the steps of:

providing a reflector for the vaporization device, wherein the reflector is positioned around the heating element; and refocusing the heat produced by the heating element onto the first portion by the reflector.

8. The method for producing oxygen-rich vapor derived from herb-based plants and extracts from said herb-based plants as claimed in claim 1, wherein a length of the first time increment is inversely proportionate to a length of the fourth time increment.

\* \* \* \* \*